US009610445B2

United States Patent
Thakur et al.

(10) Patent No.: US 9,610,445 B2
(45) Date of Patent: Apr. 4, 2017

(54) METHODS AND APPARATUS FOR DETECTING HEART FAILURE EVENT USING IMPEDANCE VECTOR SWITCHING

(71) Applicant: Cardiac Pacemakers, Inc., St. Paul, MN (US)

(72) Inventors: Pramodsingh Hirasingh Thakur, Woodbury, MN (US); Qi An, Blaine, MN (US); Viktoria A. Averina, Roseville, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 0 days.

(21) Appl. No.: 14/509,707

(22) Filed: Oct. 8, 2014

(65) Prior Publication Data
US 2015/0105835 A1  Apr. 16, 2015

Related U.S. Application Data

(60) Provisional application No. 61/891,130, filed on Oct. 15, 2013.

(51) Int. Cl.
*A61N 1/36* (2006.01)
*A61N 1/365* (2006.01)
(Continued)

(52) U.S. Cl.
CPC ...... *A61N 1/36521* (2013.01); *A61B 5/04011* (2013.01); *A61B 5/0538* (2013.01);
(Continued)

(58) Field of Classification Search
CPC .............. A61N 1/35621; A61N 1/3627; A61N 2001/083; A61B 5/04011; A61B 5/7275
(Continued)

(56) References Cited

U.S. PATENT DOCUMENTS 8,295,918 B2  10/2012  Rosenberg et al.
8,380,303 B2   2/2013  Rosenberg
(Continued)

FOREIGN PATENT DOCUMENTS

EP        2143467 A1    1/2010
WO    WO-2015057451 A1  4/2015

OTHER PUBLICATIONS

"International Application Serial No. PCT/US2014/059686, International Preliminary Report on Patentability mailed Apr. 28, 2016", 9 pgs.

(Continued)

*Primary Examiner* — Paula J Stice
(74) *Attorney, Agent, or Firm* — Schwegman Lundberg & Woessner, P.A.

(57) ABSTRACT

Devices and methods for detecting physiological target event such as events indicative of heart failure (HF) decompensation status are described. An ambulatory medical device (AMD) can detect device site maturation such as in a device encapsulation pocket, and classify the maturation status into one of two or more device site maturation states. The AMD can include an electrical impedance analyzer circuit that can measure a first maturation-insensitive impedance vector and a second maturation-sensitive impedance vector. At least one impedance vector can be selected or a composite impedance vector can be generated in accordance with the classified device site maturation state. The AMD can generate an impedance indicator using the selected or composite impedance vector, and detect a target physiologic event indicative of worsening of HF using the impedance indicator.

20 Claims, 7 Drawing Sheets

(51) Int. Cl.
    *A61N 1/362*     (2006.01)
    *A61B 5/04*     (2006.01)
    *A61B 5/053*     (2006.01)
    *A61B 5/00*     (2006.01)

(52) U.S. Cl.
    CPC ....... *A61N 1/3627* (2013.01); *A61N 1/36542* (2013.01); *A61N 1/36557* (2013.01); *A61N 1/36585* (2013.01); *A61B 5/7275* (2013.01)

(58) Field of Classification Search
    USPC .......................................................... 607/18
    See application file for complete search history.

(56) References Cited

U.S. PATENT DOCUMENTS

| | | |
|---|---|---|
| 8,473,054 B2 | 6/2013 | Pillai et al. |
| 2010/0305641 A1 | 12/2010 | Pillai et al. |
| 2012/0221066 A1* | 8/2012 | Rosenberg ........... A61N 1/3627 607/4 |
| 2013/0197381 A1 | 8/2013 | Charlton et al. |

OTHER PUBLICATIONS

"International Application Serial No. PCT/US2014/059686, International Search Report mailed Dec. 15, 2014", 4 pgs.
"International Application Serial No. PCT/US2014/059686, Written Opinion mailed Dec. 15, 2014", 7 pgs.

* cited by examiner

METHODS AND APPARATUS FOR DETECTING HEART FAILURE EVENT USING IMPEDANCE VECTOR SWITCHING

CLAIM OF PRIORITY

This application claims the benefit of priority under 35 U.S.C. §119(e) of U.S. Provisional Patent Application Ser. No. 61/891,130, filed on Oct. 15, 2013, which is herein incorporated by reference in its entirety.

TECHNICAL FIELD

This document relates generally to medical devices, and more particularly, to systems, devices and methods for detecting and monitoring events indicative of worsening of heart failure.

BACKGROUND

Congestive heart failure (CHF) is a major health problem and affects over five million people in the United States alone. CHF patients typically have enlarged heart with weakened cardiac muscles, resulting in poor cardiac output of blood. Elevated pulmonary vascular pressures can cause fluid accumulation in the lungs over time. In many CHF patients, fluid accumulation precedes episodes of heart failure (HF) decompensation. The HF decompensation can be characterized by pulmonary or peripheral edema, reduced cardiac output, and symptoms such as fatigue, shortness of breath and the like.

OVERVIEW

Frequent monitoring of CHF patients and timely detection of intrathoracic fluid accumulation or other events indicative of HF decompensation status can help prevent worsening of HF in CHF patients, hence reducing cost associated with HF hospitalization.

Ambulatory medical devices can be used for monitoring HF patient and detecting HF decompensation events. Examples of such ambulatory medical devices can include implantable medical devices (IMD), subcutaneous medical devices, wearable medical devices or other external medical devices. The ambulatory or implantable medical devices can include physiologic sensors which can be configured to sense electrical activity and mechanical function of the heart, and the medical device can optionally deliver therapy such as electrical stimulation pulses to a target area, such as to restore or improve the cardiac function. Some of these devices can provide diagnostic features, such as using transthoracic impedance or other sensor signals. For example, fluid accumulation in the lungs decreases the transthoracic impedance due to the lower resistivity of the fluid than air in the lungs.

Desirable performance of a method or a device for detecting HF decompensation can include one or more of a high sensitivity, a high specificity, or a high positive predictive value (PPV). The sensitivity can represent a percentage of actual HF decompensation episodes that are correctly recognized by a detection method. The specificity can represent a percentage of actual non-HF decompensation episodes that are correctly recognized as non-HF decompensation events by the detection method. The PPV can represent a percentage of the detected HF decompensation episodes, as declared by the detection method, which are actual HF decompensation events. A high sensitivity can help ensure timely intervention to a patient with an impending HF decompensation episode, whereas a high specificity and a high PPV can help avoid unnecessary intervention and added healthcare cost due to false alarms.

HF decompensation detection may be affected by a number of factors including the choice of physiologic sensors or physiologic signals. For example, a detector using a particular sensor signal may provide desirable accuracy in HF decompensation event detection in one patient but less sensitive or less specific in another patient. Additionally, the performance of a detector using one type of sensor signal may change over time due to patient's disease progression or development of a new medical condition. An example of such a patient disease or condition includes maturation of device-tissue interface, such as a surgically created device pocket that encapsulates an implantable medical device, or an interface between an implantable lead and tissues adjacent to a portion of the lead, including one or more electrodes along or on an end of the lead. During an acute phase following implantation of a medical device such as an implantable cardiac pacemaker or defibrillator, the electrodes or the device housing are subject to on-going tissue encapsulation around the electrodes or the device housing. When the lead electrodes and the device housing are used for sensing electrograms or other physiological signals such as intrathoracic or intracardiac impedance, the tissue encapsulation and the maturation status of the device pocket may affect the impedance signals or other physiological signals sensed from the electrodes and the device housing. This may render unreliable detection of target physiologic event such as pulmonary edema or prediction of an impending HF decompensation event. That is, physiological signals that are sensitive to device site maturation may cause undesired false positive detections of target events indicative of worsening of HF.

The device site maturation can sustain for a long duration. For example, device encapsulation pocket maturation can last up to six months following the device implant or procedures that revise the pocket. The duration of maturation process and the magnitude of impact on the sensed physiologic signals (such as thoracic impedance chronically measured using the implantable device) may vary greatly among patients. During the post-implant acute phase, patients' health conditions can be unstable and are more vulnerable to events such as HF decompensation. As such, it may not be clinically acceptable to ignore the impedance or other physiologic signals during the acute phase and initiate the HF decompensation detection only when the physiologic signals become stabilized several weeks or months following the implant or device pocket revision. Therefore, the present inventors have recognized that there remains a considerable need for improving HF decompensation events detection in CHF patients particularly during the acute phase before the device site completely matures and becomes stabilized.

Various embodiments described herein can help improve the detection of target physiologic events such as events indicative of worsening of HF or HF decompensation status. For example, an ambulatory medical device (AMD), such as an implantable or a wearable medical device, can detect an HF decompensation event, such as using an impedance indicator in accordance with the status of the device site maturation. The AMD can include an electrical impedance analyzer circuit capable of measuring from a patient first and second impedance vectors, such as thoracic impedance vectors. The first impedance vector can have a lower predicted sensitivity to the device site maturation than the second impedance vector. An impedance vector selector circuit can select at least one impedance vector from the first and the second impedance vectors using information correlative to an indication of the device site maturation, or generate a composite impedance vector using the first and the second impedance vectors. An impedance indicator generator circuit can generate an impedance indicator indicative of a target physiologic event using the selected at least one impedance vector, or the composite impedance vector. The medical device can include a physiologic event detector circuit configured to detect the target physiologic event such as an HF decompensation event using the impedance indicator.

A method of operating an ambulatory medical device in a patient can include providing information correlative to an indication of device site maturation. At least first and second impedance vectors can be measured from the patient, where the first impedance vector can have a tower predicted sensitivity to the device site maturation than the second impedance vector. The method can include selecting at least one impedance vector from the first and the second impedance vectors using the information correlative to an indication of the device site maturation. The method can include using the selected impedance vector to generate an impedance indicator indicative of a target physiologic event, and detecting the target physiologic event using the impedance indicator.

This Overview is an overview of some of the teachings of the present application and not intended to be an exclusive or exhaustive treatment of the present subject matter. Further details about the present subject matter are found in the detailed description and appended claims. Other aspects of the invention will be apparent to persons skilled in the art upon reading and understanding the following detailed description and viewing the drawings that form a part thereof, each of which are not to be taken in a limiting sense. The scope of the present invention is defined by the appended claims and their legal equivalents.

BRIEF DESCRIPTION OF THE DRAWINGS

Various embodiments are illustrated by way of example in the figures of the accompanying drawings. Such embodiments are demonstrative and not intended to be exhaustive or exclusive embodiments of the present subject matter.

DETAILED DESCRIPTION

Disclosed herein are systems, devices, and methods for detecting one or more physiologic target events or conditions. The events can include early precursors of an HF decompensation episode. That is, these events can occur well before the systematic manifestation of worsening of HF. Therefore, by detecting the precursor events, the present document can provide a system and a method of detecting an impending HF decompensation episode. In particular, the methods and devices described herein can be applicable to detecting accumulation of intrathoracic fluid that can forecast an impending HF decompensation episode. More generally, the systems, devices, and methods described herein may be used to determine HF status and/or track HF progression such as worsening of or recovery front an HF event.

Figure 1:
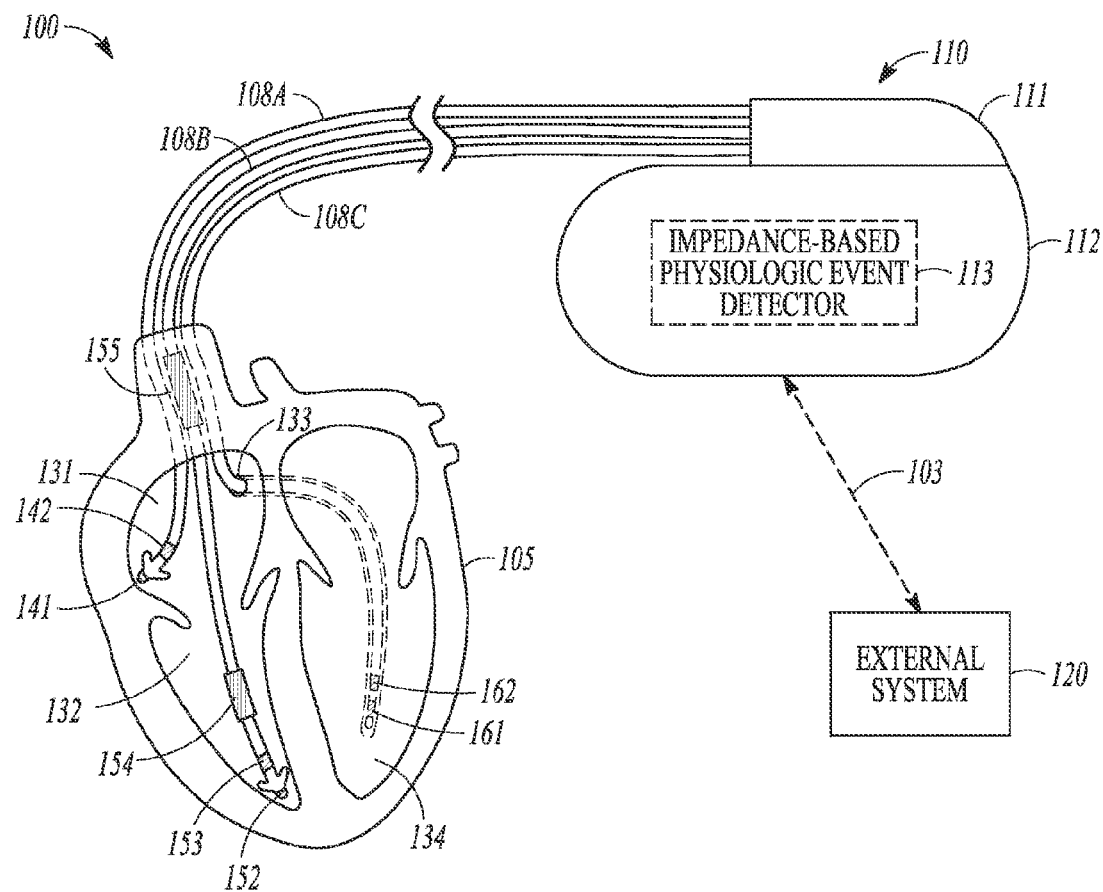
FIG. 1 illustrates an example of a cardiac rhythm management (CRM) system and portions of the environment in which the CRM system operates.

FIG. 1 illustrates an example of a Cardiac Rhythm Management (CRM) system 100 and portions of an environment in which the CRM system 100 can operate. The CRM system 100 can include an ambulatory medical device, such as an implantable medical device (IMD) 110 that can be electrically coupled to a heart 105 such as through one or more leads 108A-C, and an external system 120 that can communicate with the IMD 110 such as via a communication link 103. The IMD 110 may include an implantable cardiac device such as a pacemaker, an implantable cardioverter-defibrillator (ICD), or a cardiac resynchronization therapy defibrillator (CRT-D). The IMD 110 can include one or more monitoring or therapeutic devices such as a subcutaneously implanted device, a wearable external device, a neural stimulator, a drug delivery device, a biological therapy device, or one or more other ambulatory medical devices. The IMD 110 may be coupled to, or may be substituted by a monitoring medical device such as a bedside or other external monitor.

As illustrated in FIG. 1, the IMD 110 can include a hermetically sealed can 112 that can house an electronic circuit that can sense a physiological signal in the heart 105 and can deliver one or more therapeutic electrical pulses to a target region, such as in the heart, such as through one or more leads 108A-C. The CRM system 100 can include only one lead such as 108B, or can include two leads such as 108A and 108B.

The lead 108A can include a proximal end that can be configured to be connected to IMD 110 and a distal end that can be configured to be placed at a target location such as in the right atrium (RA) 131 of the heart 105. The lead 108A can have a first pacing-sensing electrode 141 that can be located at or near its distal end, and a second pacing-sensing electrode 142 that can be located at or near the electrode 141. The electrodes 141 and 142 can be electrically connected to the IMD 110 such as via separate conductors in the lead 108A, such as to allow for sensing of the right atrial activity and optional delivery of atrial pacing pulses. The lead 108B can be a defibrillation lead that can include a proximal end that can be connected to IMD 110 and a distal end that can be placed at a target location such as in the right ventricle (RV) 132 of heart 105. The lead 108B can have a first pacing-sensing electrode 152 that can be located at distal end, a second pacing-sensing electrode 153 that can be located near the electrode 152, a first defibrillation coil electrode 154 that can be located near the electrode 153, and a second defibrillation coil electrode 155 that can be located at a distance from the distal end such as for superior vena cava (SVC) placement. The electrodes 152 through 155 can be electrically connected to the IMD 110 such as via separate conductors in the lead 108B. The electrodes 152 and 153 can allow for sensing of a ventricular electrogram and can optionally allow delivery of one or more ventricular pacing pulses, and electrodes 154 and 155 can allow for delivery of one or more ventricular cardioversion/defibrillation pulses. In an example, the lead 108B can include only three electrodes 152, 154 and 155. The electrodes 152 and 154 can be used for sensing or delivery of one or more ventricular pacing pulses, and the electrodes 154 and 155 can be used for delivery of one or more ventricular cardioversion or defibrillation pulses. The lead 108C can include a proximal end that can be connected to the IMD 110 and a distal end that can be configured to be placed at a target location such as in a left ventricle (LV) 134 of the heart 105. The lead 108C may be implanted through the coronary sinus 133 and may be placed in a coronary vein over the LV such as to allow for delivery of one or more pacing pulses to the LV. The lead 108C can include an electrode 161 that can be located at a distal end of the lead 108C and another electrode 162 that can be located near the electrode 161. The electrodes 161 and 162 can be electrically connected to the IMD 110 such as via separate conductors in the lead 108C such as to allow for sensing of the LV electrogram and optionally allow delivery of one or more resynchronization pacing pulses from the LV.

The IMD 110 can include an electronic circuit that can sense a physiological signal. The physiological signal can include an electrogram or a signal representing mechanical function of the heart 105. The hermetically sealed can 112 may function as an electrode such as for sensing or pulse delivery. For example, an electrode from one or more of the leads 108A-C may be used together with the can 112 such as for unipolar sensing of an electrogram or for delivering one or more pacing pulses. A defibrillation electrode from the lead 108B may be used together with the can 112 such as for delivering one or more cardioversion/defibrillation pulses. In an example, the IMD 110 can sense impedance such as between electrodes located on one or more of the leads 108A-C or the can 112. The IMD 110 can be configured to inject current between a pair of electrodes, sense the resultant voltage between the same or different pair of electrodes, and determine impedance using Ohm's Law. The impedance can be sensed in a bipolar configuration in which the same pair of electrodes can be used for injecting current and sensing voltage, a tripolar configuration in which the pair of electrodes for current injection and the pair of electrodes for voltage sensing can share a common electrode, or tetrapolar configuration in which the electrodes used for current injection can be distinct from the electrodes used for voltage sensing. In an example, the IMD 110 can be configured to inject current between an electrode on the RV lead 108B and the can housing 112, and to sense the resultant voltage between the same electrodes or between a different electrode on the RV lead 108B and the can housing 112. A physiologic signal can be sensed from one or more physiological sensors that can be integrated within the IMD 110. The IMD 110 can also be configured to sense a physiological signal from one or more external physiologic sensors or one or more external electrodes that can be coupled to the IMD 110. Examples of the physiological signal can include one or more of intrathoracic impedance, intracardiac impedance, arterial pressure, pulmonary artery pressure, RV pressure, LV coronary pressure, coronary blood temperature, blood oxygen saturation, one or more heart sounds, physical activity or exertion level, posture, respiration, body weight, or body temperature.

The arrangement and functions of these leads and electrodes are described above by way of example and not by way of limitation. Depending on the need of the patient and the capability of the implantable device, other arrangements and uses of these leads and electrodes are contemplated.

As illustrated, the CRM system 100 can include an impedance-based physiologic event detector 113. The impedance-based physiologic event detector 113 can be configured to be capable of receiving first and second physiologic signals such as thoracic or cardiac impedance signals from a patient, where the first signal can have a lower predicted sensitivity to the device site maturation than the second signal. Both the first and the second impedance signals can be sensed using the electrodes on one or more of the leads 108A-C or the can 112, or other physiologic sensors deployed on or within the patient and communicated with the IMD 110. The impedance-based physiologic event detector 113 can include a circuit capable of receiving information correlative to an indication of the device site maturation. In an example, the impedance-based physiologic event detector 113 can be configured to detect the status of maturation of device-tissue interface, such as an encapsulation pocket for the IMD or a lead-tissue interface. The device encapsulation pocket can include interface between at least a portion of the can 112, and the surrounding tissue. Based on the maturation status, the impedance-based physiologic event detector 113 can select at least one impedance vector from the first and the second impedance vectors, or to generate a composite impedance vector using two or more impedance vectors. The impedance-based physiologic event detector 113 can detect a target physiologic event or condition of the patient using the selected at least one impedance vector, or the composite impedance vector. An example of the physiologic events is an HF decompensation event, which can include one or more early precursors of an HF decompensation episode or an event indicative of HF progression such as worsening of HF or recovery from an HF event. The impedance-based physiologic event detector 113 can also be configured to detect physiologic events such as pulmonary edema, myocardial infarction, among others. Examples of the impedance-based physiologic event detector 113 are described below, such as with reference to FIGS. 2-3.

The external system 120 can allow for programming of the IMD 110 and can receive information about one or more signals acquired by IMD 110, such as can be received via a communication link 103. The external system 120 can include a local external IMD programmer. The external system 120 can include a remote patient management system that can monitor patient status or adjust one or more therapies such as from a remote location.

The communication link 103 can include one or more of an inductive telemetry link, a radio-frequency telemetry link, or a telecommunication link, such as an interact connection. The communication link 103 can provide for data transmission between the IMD 110 and the external system 120. The transmitted data can include, for example, real-time physiological data acquired by the IMD 110, physiological data acquired by and stored in the IMD 110, therapy history data or data indicating IMD operational status stored in the IMD 110, one or more programming instructions to the IMD 110 such as to configure the IMD 110 to perform one or more actions that can include physiological data acquisition such as using programmably specifiable sensing electrodes and configuration, device self-diagnostic test, or delivery of one or more therapies.

The impedance rank-based physiologic event detector 113 may be implemented in the external system 120. The external system 120 can be configured to perform HF decompensation event detection such as using data extracted from the IMD 110 or data stored in a memory within the external system 120. Portions of the impedance rank-based physiologic event detector 113 may be distributed between the IMD 110 and the external system 120.

Portions of the IMD 110 or the external system 120 can be implemented using hardware, software, or any combination of hardware and software. Portions of the IMD 110 or the external system 120 may be implemented using an application-specific circuit that can be constructed or configured to perform one or more particular functions, or can be implemented using a general-purpose circuit that can be programmed or otherwise configured to perform one or more particular functions. Such a general-purpose circuit can include a microprocessor or a portion thereof, a microcontroller or a portion thereof, or a programmable logic circuit, or a portion thereof. For example, a "comparator" can include, among other things, an electronic circuit comparator that can be constructed to perform the specific function of a comparison between two signals or the comparator can be implemented as a portion of a general-purpose circuit that can be driven by a code instructing a portion of the general-purpose circuit to perform a comparison between the two signals. While described with reference to the IMD 110, the CRM system 100 could include a subcutaneous medical device (e.g., subcutaneous ICD, subcutaneous diagnostic device), wearable medical devices (e.g., patch based sensing device), or other external medical devices.

Figure 2:
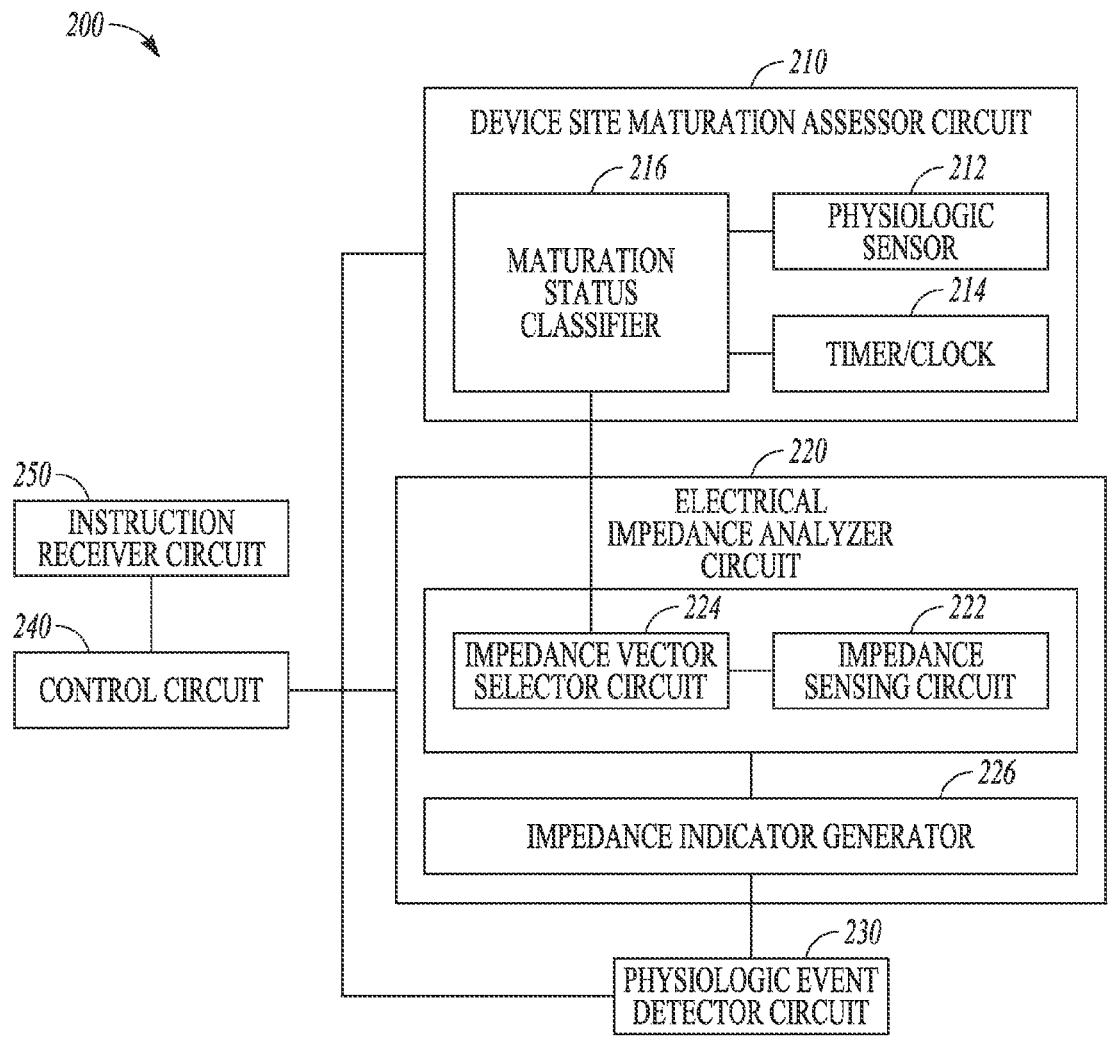
FIG. 2 illustrates an example of an impedance-based physiologic target event detector.

FIG. 2 illustrates an example of an impedance-based physiologic target event detector 200. The physiologic target event detector 200 can be an embodiment of the impedance-based physiologic event detector 113. In an example, the physiologic target event detector 200 can be configured to detect an event indicative of worsening of heart failure (HF), such as a HF decompensation event. The physiologic target event detector 200 can include one or more of a device site maturation assessor circuit 210, an electrical impedance analyzer circuit 220, a physiologic event detector circuit 230, a controller circuit 240, and an instruction receiver circuit 250.

The device site maturation assessor circuit 210 can be configured to receive information correlative to an indication of the device site maturation. In an example, the device site maturation assessor circuit 210 can assess maturation of a device-tissue interface, such as an encapsulation pocket surgically created or intervened for IMD during implantation of the IMD, or maturation of a lead/electrode and tissue (such as myocardium) interface following a lead implant or lead revision. The device site maturation assessor circuit 210 can include one or more physiologic sensors 212, a timer/clock circuit 214, and a maturation status classifier 216.

The physiologic sensor 212 can be configured to sense a physiologic signal indicative of the device site maturation state. Examples of the physiologic sensors 212 can include an impedance sensor, an acoustic sensor, an accelerometer, a temperature sensor, or a chemical sensor. A statistical or a morphological signal metric can be obtained from a physiologic signal sensed around the device encapsulation pocket or the lead-tissue interface. The signal metric value can be indicative of the amount and electrical properties of the fibrotic tissue formed within the device pocket or at the lead-tissue interface, therefore can be used to assess the degree of device site maturation. In some examples, the physiologic sensors 212 can be used to measure one or more physiologic signals that indicate the systematic health status or well-being of the patient, such as body temperature, blood pressure, or other vital signs or physiologic responses. These systematic physiologic signals can indirectly indicate the device site maturation status.

As an addition or an alternative to the physiologic sensors 212, the timer/clock circuit 214 can determine time elapsed from a reference time associated with a trigger event, such as events indicative of implantation of an IMD, device encapsulation pocket revision, lead implant or lead revision, or other specified events that may affect the device site maturation status.

The maturation status classifier 216 can categorize the device site maturation status into one of two or more device site maturation states. Examples of the device site maturation states can include an acute state, a recovery state, or a stable state. The maturation status classifier 216 can perform the categorization using the sensed physiologic signal or signal metrics calculated from the physiologic signal. For example, the sensed physiologic signal or the signal metrics can be compared to multiple thresholds that define the physiological signal values into multiple intervals or value ranges each corresponding to a maturation state.

The maturation status classifier 216 can perform the categorization using the elapsed time from a reference time associated with a trigger event. The device site maturation assessor circuit 210 can be coupled to a memory circuit that stores one or more time windows corresponding to respective maturation states. The time windows can be defined relative to the reference time associated with a specified trigger event. For example, an acute state can correspond to a time window that starts at a trigger event such as the device implant or pocket revision and lasts for specified duration, for example, up to approximately 2-4 weeks. A recovery state can correspond to a time window that starts at 2-4 weeks and ends at 4-6 months following the trigger event. A stable state can correspond to a time window that starts 4-6 months following the trigger event. The maturation status classifier 216 can classify the device site maturation into one of multiple device site maturation states when an elapse time relative to the reference time falls into one of the time windows.

In some examples, the maturation status classifier 216 can receive qualitative descriptors of the device site maturation, including subjective description or objective characterization of the device-tissue interface or patient's systematic response to the device site maturation. Examples of the qualitative descriptors can include pain, swelling, erythema or other skin conditions at or near the device-tissue interface, among others. The maturation status classifier 216 can be configured to quantize the qualitative descriptors into a multitude of levels of severity. The descriptors can also be quantized with the use of external analyzing devices by system end-users such as physicians or other health-care providers, who can feed the quantized descriptors into the maturation status classifier 216.

The electrical impedance analyzer circuit 220 can include an impedance sensing circuit 222, an impedance vector selector circuit 224, and an impedance indicator generator circuit 226. The impedance sensing circuit 222 can be coupled to one or more electrodes disposed on one or more leads 108A-C or the can 112, and can be configured to measure bio-impedance from a patient therein. The measured bio-impedance can include a plurality of thoracic impedance measurements or a plurality of cardiac impedance measurements. For example, the bio-impedance can include an impedance vector sensed between an RA electrode 141 or 142 and the can 112 ($Z_{RA-Can}$), between an RV electrode 152, 153 or 154 and a can 112 ($Z_{RV-Can}$), or between an LV electrode 161 or 162 and the can 112 ($Z_{RV-Can}$). The bio-impedance can also include an impedance vector where the voltage sensing electrodes are the currently injection electrodes are orthogonal to each other, such as selected from RA, RV, or LV electrodes ($Z_{RA\text{-}RV\text{-}LV}$). Additionally or alternatively, the electrical impedance sensing circuit 222 can be coupled to one or more implantable or wearable physiologic sensors or one or more patient monitors that can sense or receive signals indicative of the bio-impedance.

The electrical impedance sensing circuit 222 can include one or more modules to perform impedance signal conditioning such as signal amplification, digitization, or filtering. The one or more modules can be configured to extract one or more impedance signal metrics from the sensed impedance signal. The impedance signal metrics can include statistical or morphological signal features computed from the sensed impedance signal. Examples of the statistical signal features can include signal mean, median, or other central tendency measures; a histogram of the signal intensity; or one or more signal trends over time. Examples of the morphological signal features can include maximum or minimum within a specified period such as a cardiac cycle, positive or negative slope or higher order statistics, signal power spectral density at a specified frequency range, and other morphological descriptors.

The impedance sensing circuit 222 can be configured to be capable of sensing two or more impedance vectors independently or concurrently. In an example, the impedance sensing circuit 222 can sense a first impedance vector predicatively less sensitive to the progression of device site maturation and a second impedance vector predicatively more sensitive to the progression of device site maturation. The first and the second impedance vectors can have different configurations, such as using different electrodes to inject electric current or different electrodes for sensing the resulting voltage. Examples of the impedance sensing circuit 222 configured for sensing device site maturation-insensitive and device site maturation-sensitive impedance vectors are discussed below, such as with reference to FIG. 3.

The impedance vector selector circuit 224 can be configured to select at least one impedance vector from the first and the second impedance vectors. For example, as illustrated in FIG. 2, the impedance vector selector circuit 224 can be coupled to the device site maturation status classifier 216, and select the at least one impedance vector using the classified device site maturation state. Alternatively or additionally, the impedance vector selector circuit 224 can generate a composite impedance vector using two or more impedance vectors such as those sensed by the impedance sensing circuit 222. Examples of the impedance vector selector circuit 224 configured for selecting an impedance vector or generating a composite impedance vector are discussed below, such as with reference to FIG. 3.

The impedance indicator generator 226 can be configured to generate an impedance indicator (ZI) using the one or more impedance vectors such as those determined by the impedance vector selector circuit 224. The ZI can be indicative of a presence or severity of a physiological target event or a physiologic condition precipitating the target event such as an HF decompensation episode or excessive intrathoracic fluid accumulation. In an example, the impedance indicator can be an accumulated deviation of the sensed physiological signal from a reference signal over time. Examples of computing the ZI are discussed below, such as with reference to FIGS. 6-7.

The physiologic event detector circuit 230 can receive input from the electrical impedance analyzer circuit 220 and be configured to detect a physiologic target event or condition using the impedance indicator. A target event or condition can include a physiologic event indicative of an onset of a disease, worsening of a disease state, or a change of a disease state. In an example, the physiologic event detector circuit 230 can detect the presence of an event indicative of HF decompensation status. Examples of the target events can also include a worsening HF, pulmonary edema, or myocardial infarction, among others. In some examples, the physiologic event detector circuit 230 can be configured to generate a trend of the impedance indicator over a specified time period, and to detect a target physiologic event using at least the trend of the impedance indicator.

The controller circuit 240 can control the operations of the device site maturation assessor circuit 210, the electrical impedance analyzer circuit 220, the physiologic event detector circuit 230, and the data and instruction flow among these circuits. For example, the controller circuit 240 can configure the physiologic sensor 212 for sensing the status of the device site maturation. The controller circuit 240 can start the timer/clock circuit in response to a trigger event such as device implant, and provides the elapsed time to the maturation status classifier 216 for determining the maturation status. The controller circuit 240 can configure the electrical impedance sensing circuit 222 such as by determining electrodes used for injecting current and electrodes for sensing resulting voltage.

The controller circuit 240 can determine an impedance sensing and evaluation session that includes a time window defined by a specified start time or end time, or a specified duration during which the electrical impedance analyzer circuit 220 can sense and analyze the impedance measurements. The controller circuit 240 can determine the impedance sensing and evaluation session automatically upon detection of a specified physiologic event such as a change of a physiologic parameter or a change of patient physiologic condition.

The controller circuit 240 can be coupled to an instruction receiver circuit 250 to receive instructions or programming parameters, such as from an end-user, for controlling the operation of the device site maturation assessor circuit 210, the electrical impedance analyzer circuit 220, and the physiologic event detector circuit 230. Examples of the instructions may include a start time, an end time, or a duration of the impedance sensing and evaluation session; selection between physiologic sensor 212 and the timer/clock circuit 214 for determining the maturation status; configuration of impedance vectors (including electrodes or sensors used for measuring the impedance); or the parameters for physiologic event detection as used by the physiologic event detector circuit 230. The instruction receiver circuit 250 can include a user interface configured to present programming options to the end-user and receive the end-user's programming input. In an example, at least a portion of the instruction receiver circuit 250, such as the user interface, can be implemented in the external system 120. In some examples, the end-user instructions can be programmed to the device memory and retrieved by the controller circuit 240.

Figure 3:
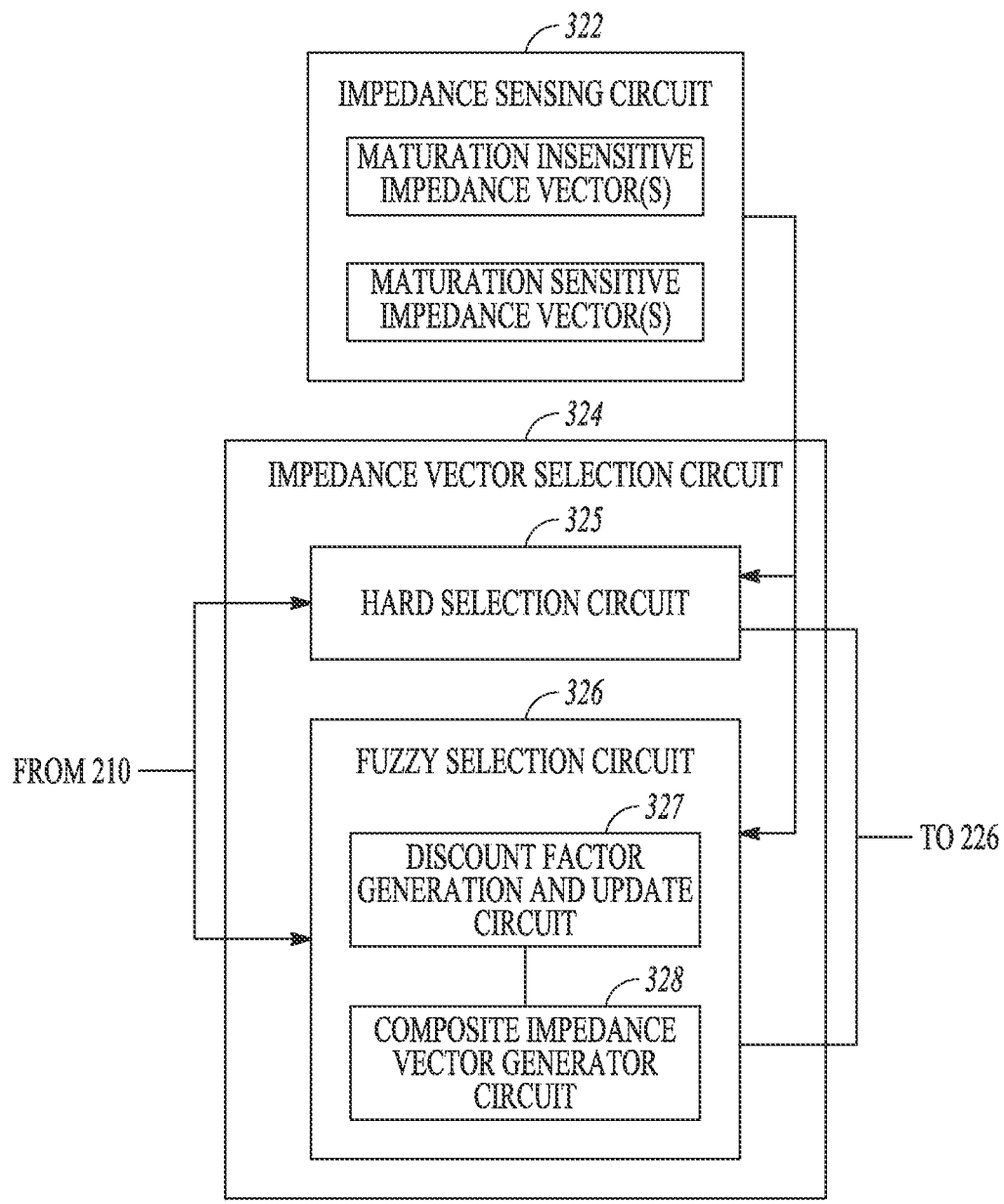
FIG. 3 illustrates an example of an impedance sensing circuit and an impedance vector selection circuit.

FIG. 3 illustrates an example of the impedance sensing circuit 322 and the impedance vector selection circuit 324. The impedance sensing circuit 322 can be an example of the impedance sensing circuit 222, and the impedance sensing circuit 324 can be an example of the impedance vector selector circuit 224.

The impedance sensing circuit 322 can be configured to be capable of measuring first and second impedance vectors independently or concurrently. The first impedance vector can have a lower predicted sensitivity to the device site maturation, than the second impedance vector. The predicted sensitivity of a particular impedance vector can be determined using data collected from a cohort of patients, such as values of the particular impedance vector in response to the maturation process of a device encapsulation pocket. Examples of the impedance vectors that are predicatively less sensitive to the device pocket maturation can include the orthogonal impedance vector ($Z_{RA-RA-LV}$) that employs a right ventricle (RV) electrode, a left ventricle (LV) electrode, and a can electrode, or impedance vectors excluding the can 112, such as impedance vectors measured between RV tip and RV ring electrodes ($RV_{tip-ring}$), between LV tip to LV ring electrodes ($LV_{tip-ring}$), or between RA tip and RV ring electrodes ($RA_{tip-ring}$), Examples of the impedance vectors that are predicatively more sensitive to device pocket maturation can include impedance vectors involving a can electrode and one of the right atrium (RA) electrode ($Z_{RA-Can}$), an RV electrode ($Z_{RV-Can}$) or an LV electrode ($Z_{LV-Can}$).

The impedance vector selection circuit 324, coupled to the impedance sensing circuit 322, can include one or both of a hard selection circuit 325 and a fuzzy selection circuit 326. The hard selection circuit 325 can select at least one impedance vector with specified configuration for impedance sensing. The hard selection circuit 325 can select between the maturation-insensitive impedance vectors and the maturation-sensitive impedance vectors according to the device site maturation status such as detected by the maturation status classifier 216. For example, the hard selection circuit 325 can select a maturation-insensitive impedance vector when the device site maturation is classified as an acute state, or to select a maturation-sensitive impedance vectors when the device site maturation is classified as a stable state. If and when the maturation status changes from one state (e.g., an acute state) to another (e.g., a stable state) during the device pocket maturation, the hard selection circuit 325 can receive from the device site maturation assessor circuit 210 the detected change of maturation states, and automatically switch from one impedance vector (e.g., a maturation-insensitive impedance vector) to another (e.g., a maturation-sensitive impedance vector).

The fuzzy selection circuit 326 can include a discount factor generation and update circuit 327 and a composite impedance vector generator circuit 328. The composite impedance vector generator circuit 328 can generate a composite impedance vector or impedance metric ($Z_{Comp}$) using at least one maturation-insensitive impedance vector ($Z_{MI}$) and at least one maturation sensitive impedance vector ($Z_{MS}$). The composite impedance vector $Z_{Comp}$ can be a linear or a non-linear combination of the $Z_{MI}$ and $Z_{MS}$. In an example, the $Z_{Comp}$ can be generated as a weighted sum of the $Z_{MI}$ and $Z_{MS}$ shown in equation (1):

$$Z_{Comp}=\alpha*Z_{MS}+\beta*Z_{MI} \quad (1)$$

where $\alpha$ and $\beta$ are weights assigned to the respective impedance vector. In some examples, the weights $\alpha$ and $\beta$ can be selected such that $\alpha+\beta=1$. This can allow $Z_{Comp}$ to have a range of value comparable to that of the $Z_{MI}$ and of the $Z_{MI}$. The impedance and the $Z_{Comp}$ can then be determined using equation (2) given below, where the weight $\alpha$ can also be referred to as a discount factor.

$$Z_{Comp}=\alpha*Z_{MS}+(1-\alpha)*Z_{MI} \quad (2)$$

The composite impedance vector generator circuit 328 can determine the $Z_{Comp}$ such as by using equations (1) or (2) according to the device site maturation status detected by, for example, the maturation status classifier 216 using a physiologic sensor response to the device site maturation or a pre-determined or user-specified time window relative to a reference time associated with a trigger event such as device implant or encapsulation pocket revision.

The discount factor generation and update circuit 327 can generate and update the discount factor $\alpha$ according to a user-input such as via the instruction receiver circuit 250. The user-specified values of $\alpha$ and corresponding classified maturation states can be stored in device memory as a look-up table, an association map, or other data structures. One example of the association between the specified values or range of values of $\alpha$ and the device site maturation states is given in the following table:

| $\alpha$ | Maturation Status |
|---|---|
| $\alpha = 0$ | Acute State |
| $\alpha = 1$ | Stable State |
| $0 < \alpha < 1$ | Recovery State |

When the device site maturation is classified using a pre-determined or user-specified time window following a trigger event such as determined by the timer/clock circuit 214, the discount factor generation and update circuit 327 can generate the discount factor $\alpha$ as a function (f) of the elapsed time (t) from the trigger event, that is, $\alpha=f(t)$. The function f can be a linear, piece-wise linear, or a non-linear function such that the value of f(t) can gradually increase from 0 to 1 as time (t) elapses. In an example, $\alpha$ can be determined using equation (3) as follows:

$$\alpha=f(t)=k\cdot t=t/T_{Stable} \quad (3)$$

where $T_{Stable}$ is the elapsed time from the trigger event until the device site maturation reaches a stable state. Therefore, as the device pocket progressively matures front the acute state to the stable state, the elapsed time (t) gradually increases from 0 to $T_{Stable}$, resulting in the discount factor gradually increases from 0 to 1.

In another example, $\alpha$ can be determined as an exponential function of the elapsed time (t) such as shown in equation (4) as follows:

$$\alpha=f(t)=\exp(\mu(t-T_{stable})) \quad (4)$$

where $\mu$ is a scalar controlling how close $\alpha$ is to 0 when t is equal to 0 (e.g., the time instant when the trigger event occurs). According to equation (4), as the device pocket progressively matures from the acute state to the stable state, the elapsed time (t) varies from 0 to $T_{Stable}$, resulting in the discount factor $\alpha$ gradually increasing from $\exp(-\mu T_{Stable})$ to 1. When the user-specified controlling scalar ($\mu$) is sufficiently large, when the device site maturation status is the acute state, the discount factor $\alpha$ can take a value approximately 0, thereby resulting a composite impedance vector $Z_{Comp}$ primarily determined by the device site maturation-insensitive impedance $Z_{MI}$. Other examples of the nonlinear function f can include sigmoid function, power function, polynomial function, radial basis function, among others. The resulting composite impedance vector or the composite impedance metric can be used for generating an impedance indicator, such as through the impedance indicator generator 226.

The discount factor generation and update circuit 327 can generate and update the discount factor $\alpha$ using maturation progression metric ($\theta$). In an example, the discount factor $\alpha$ can be a function (g) of the maturation progression metric $\theta$, that is, $\alpha=g(\theta)$. The maturation progression metric $\theta$ can be a quantitative measure of the device maturation state, and $\theta$ can be evaluated continuously or regularly such as by the maturation status classifier 216. Examples of the maturation progression metric θ can include a rate, a pattern, or other statistical or morphological signal features indicative of the progression of the device site maturation. In an example, the maturation progression metric θ can be calculated using a comparison between a temporal profile of the maturation-sensitive impedance vector and a temporal profile of the maturation-insensitive impedance vector. In another example, the maturation progression metric θ can be calculated using a comparison of the temporal profile of the impedance values of a maturation-sensitive impedance vector before and after a trigger event such as a device implant or encapsulation pocket revision. In yet another example, the maturation progression metric θ can be calculated using a comparison of the temporal profile of a maturation-sensitive impedance vector and a template signal representing a pattern of the impedance variation due to device site maturation. The template of the maturation progression can be generated using the historical impedance data before and after the trigger event from the patient.

Figure 4A:
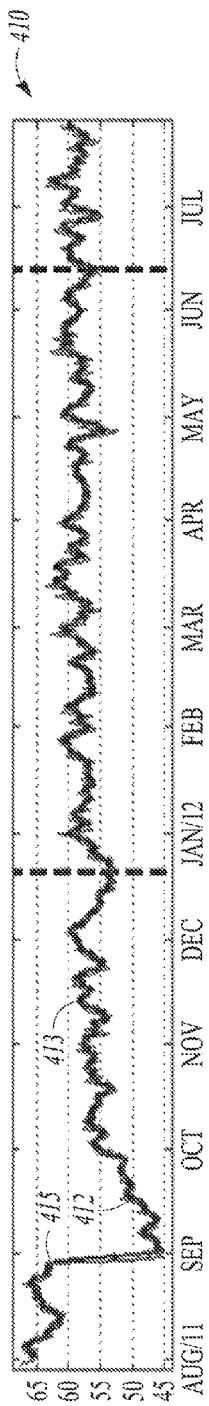
FIGS. 4A-D illustrate examples of different impedance vectors before and after a trigger event.
Figure 4B:
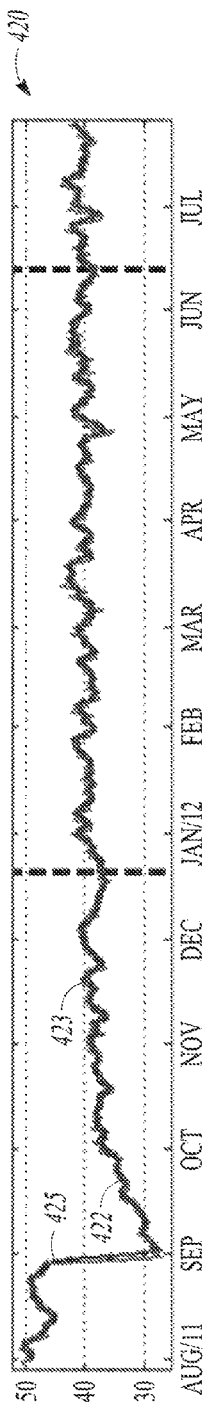
Figure 4C:
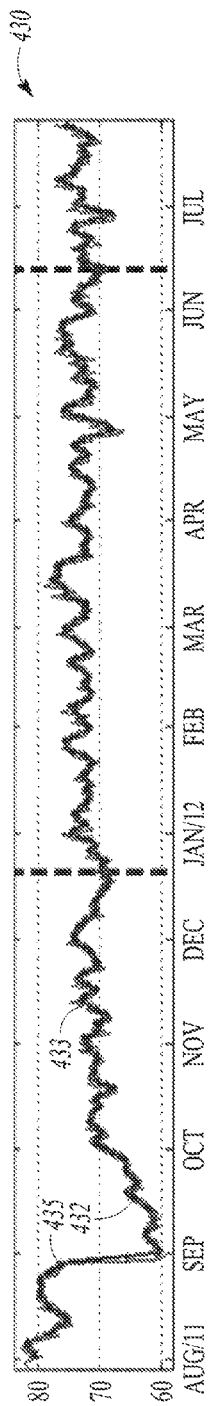
Figure 4D:
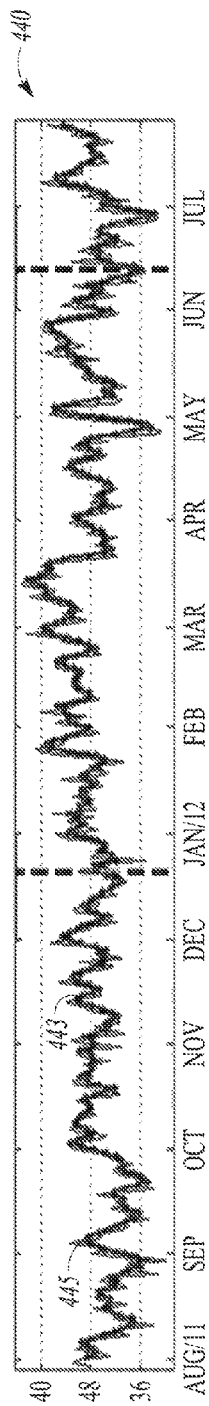

FIGS. 4A-D illustrate examples of different impedance vectors before and after a trigger event. Specifically, FIG. 4A through FIG. 4D illustrates a trend of daily median value of the intrathoracic total impedance (ITTI) measured from respectively an RA-Can vector (FIG. 4A), an RV-Can vector (FIG. 4B), the LV-Can vector (FIG. 4C), and the orthogonal RV-LV-Can vector (FIG. 4D). The four impedance vectors were concurrently sensed and recorded by an IMD from a patient. As shown in the x-axes of the FIGS. 4A-D, impedance data were measured in a time span of 12 months (from August 2011 through August 2012). A trigger event of the IMD pocket revision from sub-muscular to subcutaneous implantation site occurred around September 2011. In response to this trigger event, the daily median impedance value of the RA-Can, RV-Can and LV-Can impedance vectors all experienced decrease 415, 425 and 435 in a range of approximately 15-20 Ohms from the pre-revision to the post-revision state. Following the acute phase of impedance drop, the RA-Can, RV-Can and LV-Can impedance vectors all experience respective gradual recovery phases 412, 422, and 432 at least in part due to the progressive device site maturation. The recovery lasts approximately 1-6 months until the daily median value of the impedance vectors level off at their respective stable state 413, 423 and 433, when the chronic fibrotic tissue stably encapsulates the device in the pocket device and thus the pocket is deemed matured. Therefore, as FIGS. 4A-4D show, the RA-Can, RV-Can and LV-Can impedance vectors are all sensitive to the device site maturation.

In contrast to the impedance trends 410, 420, or 430, the daily median impedance trend 440 of the orthogonal impedance vector, as illustrated in FIG. 4D, is insensitive to the trigger event of device pocket revision. The median daily impedance value 445 changed less than two ohms in response to the trigger event, with no discernible recovery phase. The post-revision median impedance value 443 is about the same level as the pre-revision median impedance. Because of the insensitivity to the trigger event, the daily median orthogonal impedance 440 can be less prone to device site maturation than the maturation-sensitive impedance vectors. Using the orthogonal impedance 440 can therefore reduce the false positive rate of detecting events associated with worsening of HF or HF decompensation.

Figure 5:
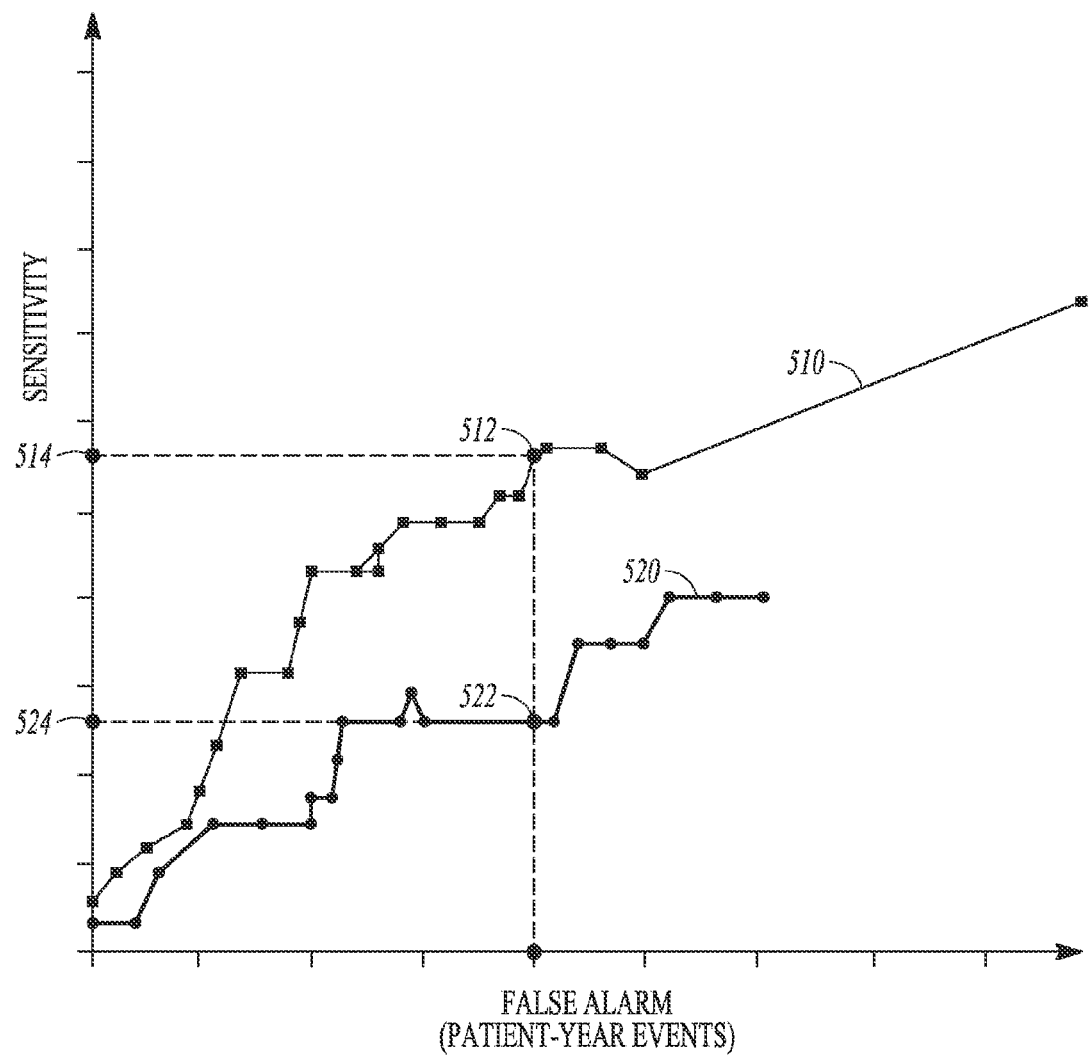
FIG. 5 illustrates examples of receiver operating characteristics (ROC) curves using various impedance vectors.

FIG. 5 illustrates examples of receiver operating characteristics (ROC) curves using various impedance vectors. The ROC curves can be used to illustrate and evaluate the performance of a detector or a detection algorithm in detecting a target physiologic event such as worsening of HF. The ROC curve depicts the sensitivities of detecting the target event (as shown in the y-axis) over the corresponding false alarm rate computed as the number of false positive detections per patient-year (as shown in the x-axis) by varying values of a detection parameter, such as threshold values associated with a detection algorithm.

Two ROC curves 510 and 520 correspond to the maturation-sensitive impedance vector $Z_{RV\text{-}Can}$ and the maturation-insensitive orthogonal impedance vector $Z_{RV\text{-}LV\text{-}Can}$, respectively. As illustrated in FIG. 5, for a specified false alarm rate, a higher sensitivity can be achieved using the ROC curve 510 than using the ROC curves 520. For example, when the false alarm rate is two events per patient-year, the corresponding operating point 512 on the ROC curve 510 corresponds to a sensitivity of approximately 55%; while at the same false alarm rate, the operating point 522 on the ROC curve 520 corresponds to a lower predicted sensitivity of approximately 25%. The area under the ROC curve ($A_{ROC}$), an index that can be used to evaluate detection performance, can be computed for the ROC curves 510 and 520. A qualitative comparison between the ROC curves 510 and 520 indicates that the $A_{ROC}$ of 510 is larger than the $A_{ROC}$ of 520. Therefore, in this example, the maturation-insensitive impedance vector $Z_{RV\text{-}Can}$ (associated with the ROC curve 510) outperforms the maturation-sensitive impedance vector $Z_{RV\text{-}LV\text{-}Can}$ (associated with the ROC curve 512).

Although the impedance vector $Z_{RV\text{-}Can}$ generally has a better detection performance, FIG. 4B illustrates that $Z_{RV\text{-}Can}$ can be sensitive to trigger events such as pocket revision or device implant, and susceptible to the subsequent device site maturation process. Therefore, although maturation-insensitive impedance vector such as $Z_{RV\text{-}LV\text{-}Can}$ is desirable during the acute state and recovery state following events like device pocket revision, when the pocked gets matured, it is desirable to switch the impedance vector from a maturation-insensitive impedance vector such as the $Z_{RV\text{-}LV\text{-}Can}$ vector to a maturation-sensitive impedance vector such as $Z_{RV\text{-}Can}$ vector to achieve desirable detection performance.

Figure 6:
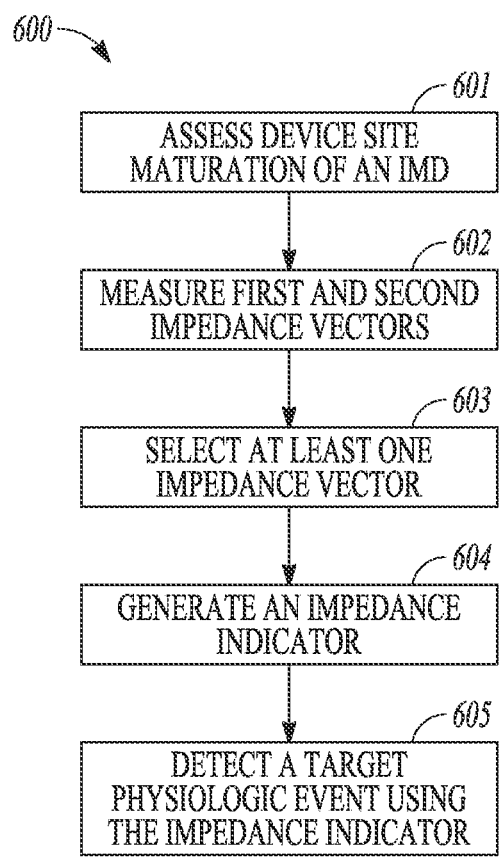
FIG. 6 illustrates an example of a method for detecting a target physiologic event using a physiologic signal such as a bio-impedance signal.

FIG. 6 illustrates an example of a method 600 for detecting a target physiologic event using a physiologic signal such as a bio-impedance signal. The target physiologic event can include events indicative of worsening of HF or HF decompensation. In an example, the method 600 can be implemented and operate in an ambulatory medical device (AMD) such as an implantable or wearable device, or in a remote patient management system. For example, the method 600 can be performed by the impedance-based physiologic event detector 113 implemented in the IMD 110, or the external system 120 in communications with the IMD 110.

At 601, a device site including a device-tissue interface is assessed to determine a maturation status. The device-tissue interface can include an encapsulation pocket for implantation of a medical device, or a lead-tissue interface between electrodes on a lead connected to the device and the tissue adjacent to the electrode. The maturation status can be evaluated using one or more indications of tissue trauma, fluid in the pocket, inflammation status, or fibrotic tissue formation in the pocket. In an example, a physiologic sensor can be used to detect a signal indicative of the device site maturation. Examples of the physiologic sensor can include an impedance sensor, an accelerometer, a temperature sensor, or a chemical sensor. Alternatively or additionally, the device site maturation status can be evaluated using the time elapsed from a reference time instant associated with a trigger event, such as an event indicative of implantation of an IMD, device pocket revision, lead implant or lead revision, or any specified event that may affect the device-tissue interface and cause maturation on a device site. For example, an acute state can correspond to a time window starting at the trigger event such as the device implant or pocket revision and lasting up to approximately 2-4 weeks. A recovery state can correspond to a time window that starts at approximately 2-4 weeks following the trigger event and ends at approximately 4-6 months following the trigger event. A stable state can correspond to a time window that starts 4-6 months following the trigger event. The device site maturation can be evaluated using subjective description or objective characterization of the device-tissue interface or patient's systematic response to the device site maturation, such as pain, swelling, erythema or other skin conditions at or near the device-tissue interface, among others.

At 602, at least first and second bio-impedance signals can be measured from the patient. The bio-impedance signals can be sensed using one or more electrodes on one or more of the implantable leads such as 108A-C or the can 112 implanted or otherwise attached to the patient. The measured bio-impedance can include a plurality of thoracic or cardiac impedance measurements. The measured bio-impedance can be processed, and the impedance metrics such as statistical or morphological signal features can be generated from the measured bio-impedance signal. The bio-impedance signal can be sensed during an impedance sensing and evaluation session.

The first and second impedance vectors can have different configurations, such as different electrodes used for injecting current or different electrodes used for sensing the resulting voltage. The first impedance vector can have a lower predicted sensitivity to the device site maturation than the second impedance vector. The predicted sensitivity of an impedance vector can be empirically determined using historical data collected from a population of patients. Examples of the impedance vectors that are predicatively less sensitive to the device pocket maturation can include the orthogonal impedance vector ($Z_{RA-RV-LV}$) or impedance vectors excluding the can 112, including impedance vectors measured between RV tip and RV ring electrodes ($RV_{tip-ring}$), between LV tip to LV ring electrodes ($LV_{tip-ring}$), or between RA tip and RV ring electrodes ($RA_{tip-ring}$). Examples of the impedance vectors that are predictably more sensitive to device site maturation can include $Z_{RA-Can}$, $Z_{RV-Can}$, or $Z_{LV-Can}$ vectors.

At 603, at least one impedance vector can be selected from the first and the second impedance vectors using at least the maturation status information such as determined at 601. In an example, a maturation-insensitive impedance vector can be selected when the device site maturation is classified as an acute state, or a maturation-sensitive impedance vector can be selected when the device site maturation is classified as a stable state. In another example, two or more impedance vectors, such as the first and the second impedance vectors, can be selected and a composite impedance vector can be created using the two or more impedance vectors. Examples of creating a composite impedance vector are discussed below, such as with reference to FIG. 7.

At 604, an impedance indicator (ZI) can be calculated from the selected impedance vector. Values of the selected impedance vector can be trended over time. A first representative impedance can be generated using impedance values measured during a first time window, and a second representative impedance can be generated using impedance values measured during a second time window. The first and the second representative impedance can each include a mean, a median, a mode, a percentile, or other measures of central tendency of the impedance values in the respective time windows. In some examples, the second time window can be longer than the first window, and at least a portion of the second time window precedes the first time window in time. The second representative impedance can be indicative of an impedance baseline ($Z_{Baseline}$). In some examples, the second time window is a moving window and $Z_{Baseline}$ can be adaptively updated such as using a linear combination of the $Z_{Baseline}$ computed from an old window and the impedance values in a new window.

The impedance indicator (ZI) can be generated using a comparison of the first representative impedance and the second representative impedance. The ZI can indicate presence or severity of a physiologic condition precipitating an HF decompensation episode, such as excessive intrathoracic fluid accumulation. The ZI can be computed as the difference, percentage difference, or other relative difference between the first representative impedance ($Z_{STV}$) of the first short-term window and the second representative impedances ($Z_{Baseline}$) of the second long-term window. That is, $ZI=Z_{Baseline}-Z_1$, or $ZI=(Z_{Baseline}-Z_{STV})/Z_{Baseline}$. The ZI can also be computed as a rate of change from the second representative impedance to the first representative impedance. That is, $ZI=(Z_{STV}-Z_{Baseline})/\Delta T_{STV\_Baseline}$, where $\Delta T_{STV\_Baseline}$ represents the time lag between the first and the second time windows.

At 605, a target physiologic event can be detected using at least the impedance indicator. A target event, such as an event indicative of worsening of HF, can be detected if the ZI meets a specified condition such as the value of ZI exceeding a specified threshold. For example, a large ZI can be indicative of substantial decrease of representative impedance from the baseline impedance, suggesting an increased thoracic fluid accumulation that is associated with worsening of HF.

Figure 7:
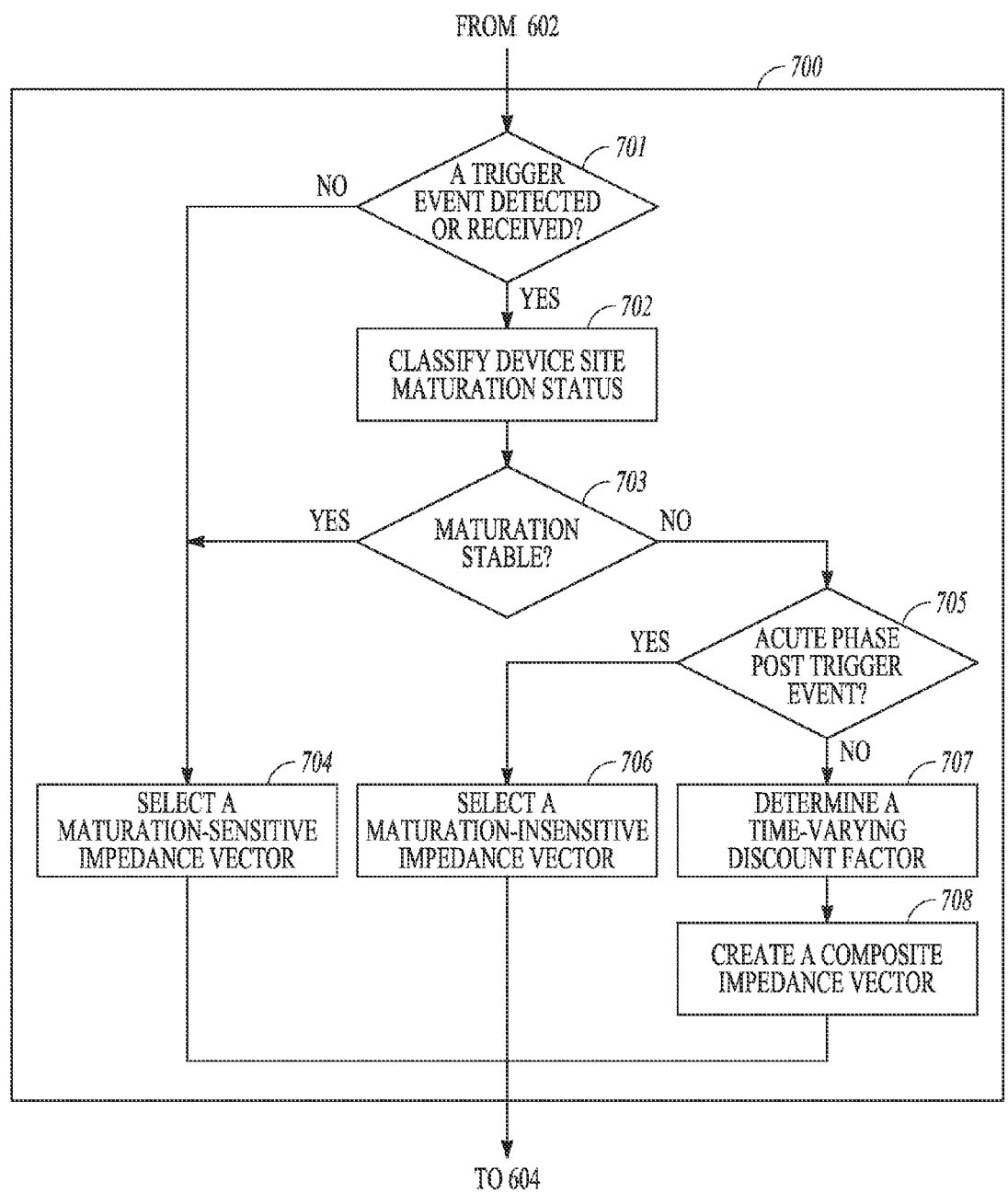
FIG. 7 illustrates an example of a method for selecting an impedance vector for detecting an event indicative of worsening of HF or HF decompensation.

FIG. 7 illustrates an example of a method 700 for selecting an impedance vector used for detecting a target physiologic event such as an event indicative of worsening of HF or HF decompensation. The method 700 can be an example of 603 as used in the method 600 for detecting the target physiologic event. In an example, the method 700 can be performed by the impedance vector selector circuit 224 as illustrated in FIG. 2, or the impedance vector selection circuit 324 as illustrated in FIG. 3.

At 701, a detection is performance to determine whether a trigger event has occurred, or if an indicator of occurrence of a trigger event has been received within a specific time frame. The trigger event can be an event indicative of a change of patient physiologic condition which may impact the electrical property of the device-tissue interface such as the impedance around the device encapsulation pocket or lead-tissue interface. Examples of the trigger event can include implantation of a medical device or surgical revision of a device encapsulation pocket. The trigger event can be detected by a sensor, or the information regarding the trigger event can be provided by an end-user such as a physician or a health-care provider. The time window to check the recent or past trigger event can be pre-determined. In one example, the time window can be approximately six months.

If no trigger event is detected or received within the specified window at 701, the device site can be deemed undisturbed and remaining stable, and a maturation-sensitive impedance vector can be selected at 704 for use in detecting the target physiologic event. As illustrated in FIG.

5, the maturation-sensitive impedance vector, such as $Z_{RA\text{-}Can}$, $Z_{RV\text{-}Can}$, or $Z_{LV\text{-}Can}$ vectors, can have a better detection performance than maturation-insensitive impedance vector when the device site maturation status is stable. Therefore, the maturation-sensitive impedance vector can be selected at 704.

If a trigger event is detected or received within the specified window at 701, then the device site maturation can be classified at 702. The device site maturation status can be classified into one of two or more states indicating the degree of maturation of the pocket. The classification can be performed using the sensed physiologic signal or the signal metrics derived from the physiologic signal, such as those used for assessing the maturation status at 601. For example, the sensed physiologic signal value or the signal metrics value can be compared to multiple thresholds that categorize the physiological signal values into multiple intervals or value ranges each corresponding to a maturation state.

If the maturation status is classified as stable state at 703, then a maturation-sensitive impedance vector can be selected at 704 for use in detecting a target physiologic event. Otherwise, at 705, the device site is checked to determine if it is in an acute phase following the trigger event. The acute phase can be determined using the sensed physiologic signal indicative of the device site maturation status. Additionally or alternatively, the acute phase can be determined using the time elapsed from the trigger event. For example, an acute state can correspond to a time window starting at the trigger event such as the device implant or pocket revision and lasting for up to approximately 2-4 weeks.

If the device site maturation status is in the acute phase, then at 706, a maturation-insensitive impedance vector, such as the orthogonal impedance vector $Z_{RV\text{-}LV\text{-}Can}$ or an impedance vector excluding a can electrode such as the can 112, can be selected. When the device site such as the device encapsulation pocket is in the process of healing, the maturation-sensitive impedance vectors can be significantly impacted and the impedance measurements therein may not reliably indicate occurrence of the target physiologic event. Using maturation-insensitive impedance vector during the acute phase of the device site maturation (rather than a maturation-sensitive impedance vector) can reduce the false positive rate in detecting events of worsening of HF.

If it is determined at 705 that the device site maturation is in a recovery phase before a stable maturation state is reached, a time-varying discount factor can be determined at 707. The discount factor determines the weight assigned to an impedance vector used for detecting the target physiologic event during the pocket recovery phase. In an example, a first time-varying discount factor can be generated for a maturation-insensitive impedance vector, and a second time-varying discount factor can be generated for a maturation-sensitive impedance vector. The first time-varying discount factor can decrease over time, and/or the second time-varying discount factor can increase over time. The first or the second time-varying discount factor can be a linear, piece-wise linear, or nonlinear function of the time elapsed from a trigger event such as device implantation or device pocket revision. Examples of the nonlinear function can include exponential function, sigmoid function, power function, polynomial function, radial basis function, among others. In an example, the time-varying discount factor can be determined using a maturation progression metric including a rate, a pattern, or other statistical or morphological signal features indicative of the progression of the device site maturation. In one example, the maturation progression metric can be calculated using a comparison between a temporal profile of the maturation-sensitive impedance vector and a temporal profile of the maturation-insensitive impedance vector.

At 708, a composite impedance vector can be generated using two or more impedance vectors. The composite impedance vector can be a weighted combination of a maturation-insensitive impedance vector and a maturation-sensitive impedance vector, each weighted by a respective discount factor. The resulting composition impedance vector can be used to generate a impedance indicator at 604 to detect the target physiologic event at 605.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, in an example, the code can be tangibly stored on one or more volatile, non-transitory, or non-volatile tangible computer-readable media, such as during execution or at other times. Examples of these tangible computer-readable media can include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. §1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

What is claimed is:

1. A system, comprising:
an ambulatory medical device (AMD) including:
an electrical impedance analyzer circuit, including:
an impedance sensing circuit configured to be capable of measuring from a patient first and second impedance vectors, the first impedance vector having a lower predicted sensitivity to device site maturation than the second impedance vector;
an impedance vector selector circuit configured to select the first impedance vector during device site maturation, and to select the second impedance vector once device site maturation has occurred; and
an impedance indicator generator circuit configured to generate an impedance indicator indicative of a target physiologic event using the selected first impedance vector during the device site maturation, and using the selected second impedance vector after the device site maturation has occurred; and
a physiologic event detector circuit coupled to the electrical impedance analyzer circuit, the physiologic event detector configured to predict or detect the target physiologic event using the impedance indicator.

2. The system of claim 1, comprising a device site maturation assessor circuit configured to produce the information correlative to the indication of the device site maturation, wherein producing the information includes classifying the device site maturation into one of two or more device site maturation states, and wherein the impedance vector selector circuit is configured to select at least one impedance vector corresponding to the classified device site maturation state.

3. The system of claim 2, wherein the device site maturation assessor circuit is configured to assess the device site maturation including maturation of at least one of an encapsulation pocket for the AMD or a lead-tissue interface, the encapsulation pocket including interface between at least a portion of a housing of the AMD and tissue adjacent to the housing of the AMD.

4. The system of claim 2, comprising a physiologic sensor configured to sense at least one physiologic signal indicative of the device site maturation state, wherein the device site maturation assessor circuit is configured to assess the device site maturation using the sensed at least one physiologic signal.

5. The system of claim 4, wherein the physiologic sensor includes one or more of an impedance sensor, an acoustic sensor, an accelerometer, a temperature sensor, or a chemical sensor.

6. The system of claim 2, wherein:
the device site maturation assessor circuit is configured to classify the device site maturation into one of two or more of an acute state, a recovery state, or a stable state; and
the impedance vector selector circuit is configured to select the first impedance vector from a set of maturation insensitive impedance vectors in response to the device site maturation being classified as the acute state, to select the second impedance vector from a set of maturation sensitive impedance vectors in response to the device site maturation being classified as the stable state, or to select both the first and the second impedance vectors in response to the device site maturation being classified as the recovery state.

7. The system of claim 6, wherein:
the set of maturation insensitive impedance vectors includes one of an orthogonal impedance vector, or an impedance vector excluding the can electrode, the orthogonal impedance vector involving a right ventricle (RV) electrode, a left ventricle (LV) electrode, and a can electrode; and
the set of maturation sensitive impedance vectors includes an impedance vector involving a can electrode and one of the right atrium (RA) electrode, an RV electrode or an LV electrode.

8. The system of claim 1, wherein the impedance indicator generator circuit is configured to generate an impedance indicator indicative of a worsening of heart failure (HF), and the physiologic event detector is configured to detect the worsening of HF using the generated impedance indicator.

9. The system of claim 1, comprising a memory circuit configured to store one or more parameters defining one or more time windows relative to a reference time, the one or more time windows each correlative to a respective device site maturation state, and wherein the impedance vector selector circuit is configured to select at least one of the first and second impedance vectors when a time relative to the reference time falls into at least one of the one or more time windows.

10. The system of claim 9, wherein the reference time includes time of an event indicative of revision of the encapsulation pocket for the AMD.

11. The system of claim 1, wherein:
the impedance vector selector circuit includes an impedance fusion circuit configured to generate a composite impedance vector using at least one maturation insensitive impedance vector and at least one maturation sensitive impedance vector; and
the impedance indicator generator circuit is configured to generate an impedance indicator using the composite impedance vector in response to the device site maturation being classified as a specified maturation state.

12. The system of claim 11, wherein the impedance fusion circuit is configured:
to determine respective weights for the at least one maturation insensitive impedance vector and the at least one maturation sensitive impedance vector; and to generate a weighted combination of the at least one maturation insensitive impedance vector and the at least one maturation sensitive impedance vector using the respective weights.

13. The system of claim 12, wherein the impedance fusion circuit is configured to determine the respective weights as a function of time.

14. A method of operating an ambulatory medical device (AMD) in a patient, the method comprising:
- receiving, at the AMD, information correlative to an indication of device site maturation;
- measuring, via the AMD, from the patient at least first and second impedance vectors, the first impedance vector having a lower predicted sensitivity to the device site maturation than the second impedance vector;
- selecting, via the AMD, the first impedance vector during device maturation, and selecting the second impedance vector once device site maturation has occurred;
- generating, via the AMD, an impedance indicator indicative of a target physiologic event using the selected first impedance vector during the device site maturation, and using the selected second impedance vector after the device site maturation has occurred; and
- predicting or detecting, via the AMD, the target physiologic event using the impedance indicator.

15. The method of claim 14, comprising assessing device site maturation including maturation of a device-tissue interface, wherein:
- assessing the device site maturation includes classifying the device site maturation into one of two or more device site maturation states; and
- receiving the information includes receiving the classified device site maturation state.

16. The method of claim 15, wherein:
assessing the device site maturation includes classifying the device site maturation into one of two or more of an acute state, a recovery state, or a stable state; and
selecting at least one impedance vector includes:
- selecting the first impedance vector from a set of maturation insensitive impedance vectors in response to the device site maturation being classified as the acute state;
- selecting the second impedance vector from a set of maturation sensitive impedance vectors in response to the device site maturation being classified as the stable state;
- or generating a composite impedance vector using at least one maturation insensitive impedance vector and at least one maturation sensitive impedance vector in response to the device site maturation being classified as the recovery state.

17. The method of claim 16, wherein generating the composite impedance vector includes:
- determining a first discount factor for the first impedance vector and a second discount factor for the second impedance vector; and
- generating a weighted combination of the first and the second impedance vectors each weighted with respective discount factor; and
- wherein generating the impedance indicator includes generating an impedance indicator using the composite impedance vector.

18. The method of claim 17, wherein:
- determining the first discount factor includes determining a first time-varying discount factor as a first function of time; and
- determining the second discount factor includes determining a second time-varying discount factor as a second function of time.

19. The method of claim 17, wherein determining the first and the second discount factors includes:
- calculating a recovery characteristic of the maturation sensitive impedance vector; and
- decreasing the first discount factor or increasing the second discount factor using the calculated recovery characteristic.

20. The method of claim 14, wherein the selection of at least one impedance vector includes selecting at least the first or at least the second impedance vector further using time elapsed from an event of revision of an encapsulation pocket for the AMD.

* * * * *